United States Patent [19]

Niina et al.

[11] Patent Number: 4,744,037

[45] Date of Patent: May 10, 1988

[54] POLYNUCLEOTIDE SYNTHESIZING APPARATUS

[75] Inventors: Akihiko Niina, Yokohama; Harumi Kamimoto, Kamakura, both of Japan

[73] Assignee: Nippon Zeon Co. Ltd., Tokyo, Japan

[21] Appl. No.: 754,755

[22] Filed: Jul. 15, 1985

[30] Foreign Application Priority Data

Jul. 20, 1984 [JP] Japan ................... 59-149642

[51] Int. Cl.$^4$ .................. G06F 15/46; C12N 15/00
[52] U.S. Cl. .................. 364/497; 364/500; 364/510; 536/27; 536/28
[58] Field of Search ............ 364/497, 500, 510; 935/87, 88; 435/317; 365/52, 72

[56] References Cited

U.S. PATENT DOCUMENTS

| | | | |
|---|---|---|---|
| 3,557,077 | 1/1971 | Brunfeldt | 530/334 |
| 3,800,288 | 3/1974 | Russell et al. | 364/200 |
| 4,217,647 | 8/1980 | Sjoholm et al. | 364/510 |
| 4,254,460 | 3/1981 | Achter et al. | 364/497 |
| 4,353,989 | 10/1982 | Bender et al. | 435/317 |
| 4,424,559 | 1/1984 | Lorincz et al. | 364/500 |
| 4,468,742 | 8/1984 | Jenden et al. | 364/497 |
| 4,483,964 | 11/1984 | Urdea et al. | 435/317 |
| 4,502,130 | 2/1985 | Kuckuk | 365/52 |
| 4,517,338 | 5/1985 | Urdea et al. | 935/88 |
| 4,589,072 | 5/1986 | Arimatsu | 364/500 |
| 4,616,308 | 10/1986 | Morshedi et al. | 364/500 |
| 4,623,968 | 11/1986 | Niese | 364/500 |

Primary Examiner—Parshotam S. Lall
Assistant Examiner—Kevin J. Teska
Attorney, Agent, or Firm—Murray and Whisenhunt

[57] ABSTRACT

A polynucleotide synthesizing apparatus comprising a storing section for storing fluid chemicals, including nucleotide reagents, solvents and the like, necessary for polynucleotide synthesis, a reactor in which the fluid chemicals react to effect the polynucleotide synthesis, a fluid supply and discharge arrangement for supplying the fluid chemicals in the storing section to the reactor and for discharging fluid chemicals from the reactor, and a control device for controlling the fluid supply and discharge arrangement. The control device comprises a programmable controller including a storage unit in which supply amount and supply/discharge sequence information for the fluid chemicals is stored. The apparatus also comprises a memory pack comprising semiconductor memory devices in which a control program and/or maintenance program is stored. The memory pack is replaceable with the storage unit of the programmable controller.

6 Claims, 6 Drawing Sheets

POLYNUCLEOTIDE SYNTHESIZING APPARATUS

BACKGROUND OF THE INVENTION

The present invention relates to a polynucleotide synthesizing apparatus used for synthesis of deoxyribonucleic acid (DNA) and ribonucleic acid (RNA) and the like.

A process for synthesizing DNA using a support to which a nucleoside is chemically bonded and successively condensing nucleotides by using the phosphite, triester phosphite and diester phosphite methods is well known. In this synthesis process, the steps of washing, deprotection, washing, condensation reaction, and washing and the like are repeated. Accordingly, the number of repetitions is high and the operation is troublesome in spite of the small number of steps.

Recently, various automatic DNA synthesizing apparatuses have been proposed for the purpose of eliminating the complexity of the synthesis operation.

The automatic DNA synthesizing apparatuses which have heretofore been proposed are adapted to be controlled by means of a microcomputer having a 128 to 512 k bit system memory and a 128 to 512 k bit user memory. However no sequence controller has been used to control the proposed polynucleotide synthesizing apparatus, since it has been found impossible for prior art sequence controllers to carry out control of the automatic DNA synthesizing apparatus, and this has been accomplished by a compact and economical programmable controller. While the programmable controller makes sophisticated control possible, the synthesizing apparatus is more bulky and more expensive than a synthesizing apparatus using microcomputer. Therefore no efforts have been made for practical use.

Since removal of a housing for incorporation of the controller using the afore-mentioned versatile microcomputer into the synthesizing apparatus will influence the reliability etc., the controller should be mounted on the housing of the synthesizing apparatus. This makes the housing of the entire apparatus more bulky. In addition, an interface for connection of the microcomputor with the synthesizing apparatus, relay devices for controlling the liquid charge and discharge means, a noise elimination device, and power regulator etc are required. Furthermore special specification of these interfaces causes high cost.

Although a controller using a dedicated P.C. board enables the entire apparatus to be compact, the board itself should be specially designed and the afore-mentioned interface is required, thereby involving high cost. Research and development cost is required whenever the P.C. board itself should be converted for modifying the program.

In other words, utilization of the microcomputer as a controller in view of the convenience of the microcomputer not only makes the synthesizing apparatus more bulky and expensive, but also sophisticated operation peculiar to the computer is required.

SUMMARY OF THE INVENTION

The present invention was made under the afore-mentioned circumstances. It is an object of the present invention to provide an automatic polynucleotide synthesizing apparatus aiming at reduction in size and cost of the apparatus, and improvement in operability.

Recent developments of sequence controllers are rapid and drastic. Rotary drum, pin board, contact micro relay and non-contact solid state type sequence controllers have successively been developed. Stored-program type controllers, or programmable controllers, in which the user of the sequence controller has made a program, are generally viewed as older-fashioned in comparison to effecting control using a microcomputer. However, programmable controllers having a 32 to 96 k bit system memory and a 2 to 32 k bit user memory have been recently developed. Therefore, the inventors have studied the possibility of incorporating an unproposed programmable controller as a main control, comprising IC, LSI, RAM and ROM and the like which is compact in size, is easy to change the stored program and is adapted to sophisticated sequence control. As a result of this, we have made the present invention in which the afore-mentioned problems are solved by using a programmable controller.

That is, the present invention resides in a polynucleotide synthesizing apparatus comprising a storing section for storing fluid chemicals including raw materials, reagents, solvents and the like which are necessary for polynucleotide synthesis; a reactor to synthesize the raw material therein; fluid supply and discharge means for supplying the fluid chemicals in the storing section to the reactor and for discharging the reagents and the solvents from the reactor; and control means for controlling the fluid supply and discharge means, the control means comprising a programmable controller including a storage unit in which the supply amount and supply discharge sequence of the fluid chemicals are stored, the fluid supply and discharge means being controlled in accordance with the contents stored in the storage unit. The programmable controller is connected with a base sequence input unit which appoints the supply order of the raw material. The liquid supply and discharge means are controlled in accordance with the contents stored in the storage unit and the appointed contents of the base sequence input unit.

In accordance with the present invention, no interfaces are required and incorporation of the controller mounted on the housing is not necessary, thereby enabling reduction in cost and size of the entire apparatus. Furthermore, the controlled contents can readily be changed by changing the stored contents in the storage unit or the appointed contents in the base sequence input unit, thereby enabling improvement in operability.

Since the programmable controller is controlled by a dedicated language, it makes it possible to provide a compact and economical sophisticated DNA synthesizing apparatus using a programmable controller which has been considered more conventional than a microprocessor. IC such as 8061, 8085, 6008 and the like may be used as CPU. 32 to 96 k bit ROM, PROM is preferable as the system memory. 2 to 32 k bit ROM, PROM, EPROM is preferable as the user memory. Use of floppy disc or magnetic tape per se as the user memory or system memory is not preferable. A timer/counter having about 30 to 200 is preferable. Input/output marks are preferably about 20 to 64 in total. Inner relays using no IC, LSC, including relay contacts are not preferable.

BRIEF DESCRIPTION OF THE DRAWINGS

FIG. 8 is a cross-sectional view showing a filter; and

DESCRIPTION OF THE PREFERRED EMBODIMENTS

The present invention will be described by way of an embodiment with reference to the accompanying drawings.

Figure 1:
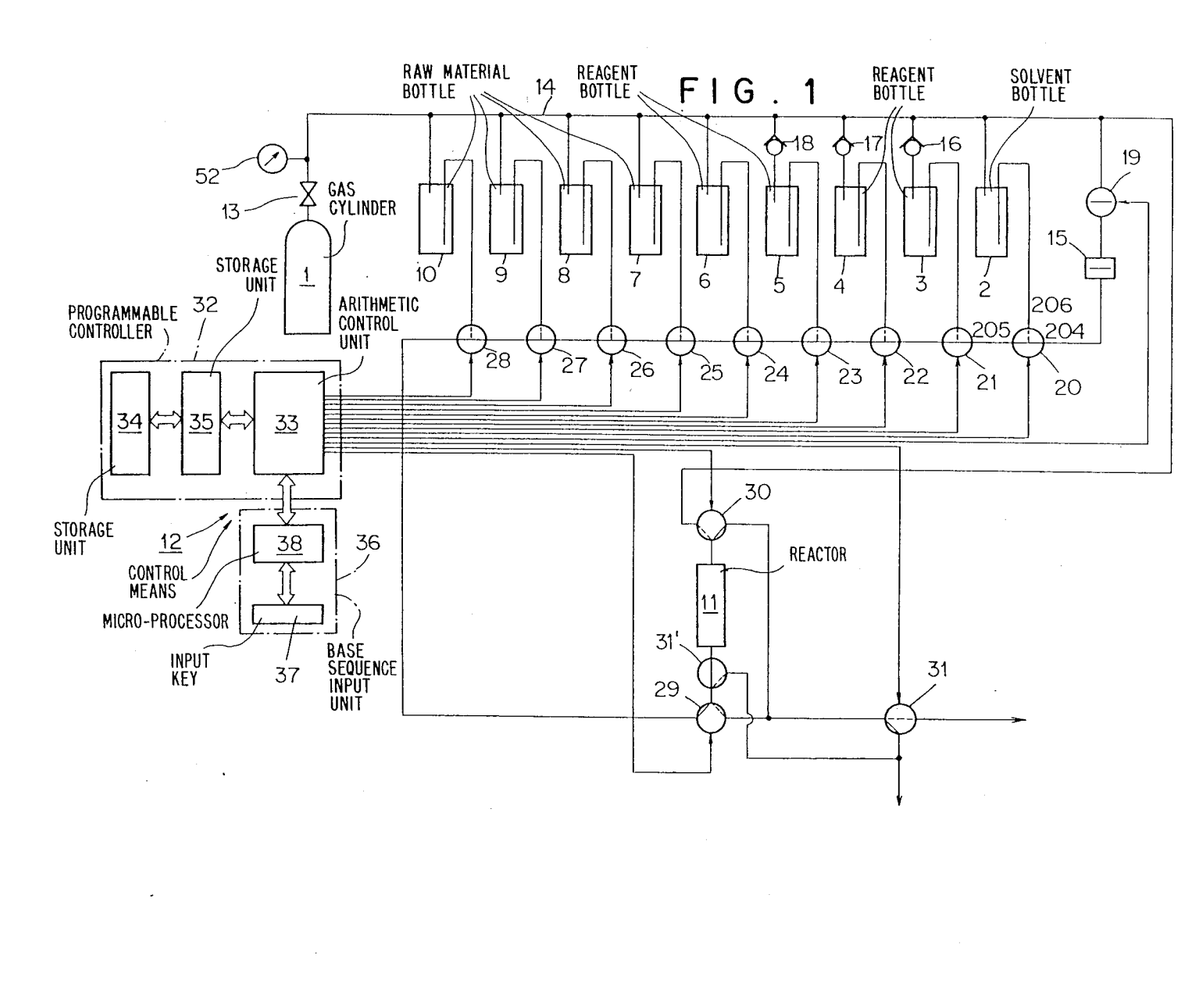
FIG. 1 is a schematic diagram showing, in its entirety, the apparatus of the present invention.
Figure 2:
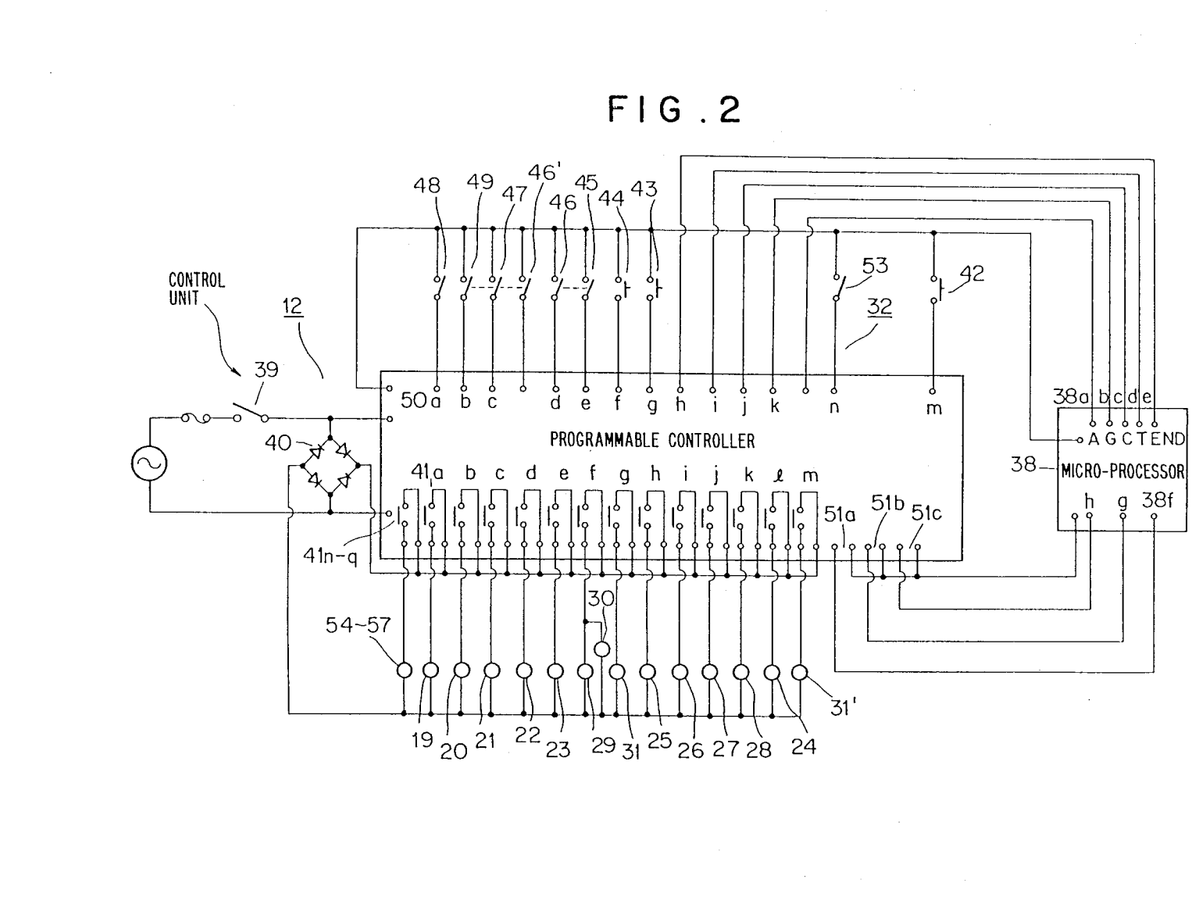
FIG. 2 is a wiring diagram showing a peripheral circuit of a programmable controller.

FIG. 1 is a schematic diagram showing an embodiment of a polynucleotide synthesizing apparatus of the present invention. FIG. 2 is a schematic diagram showing a control means in detail. In the drawings, reference numeral 1 represents an inert gas (nitrogen) cylinder, 2 a solvent bottle, 3 to 6 reagent bottles, 7 to 10 bottles containing raw materials including nucleotide reagents, 11 a reactor, and 12 a control means. The inert gas cylinder 1 and bottles 2 through 10 constitute a storing section for storing fluid chemicals including raw materials, reagents, solvents and the like.

$N_2$ gas in the nitrogen cylinder 1 is introduced into the solvent bottle 2, reagent bottles 3 to 6, and raw material bottles 7 to 10 via a regulator valve 13 and passage 14, so that solvents, reagents and raw materials are fed to the reactor 11 from the solvent bottle 2, reagent bottles 3 to 6, and raw material bottles 7 to 10 respectively under pressure of the $N_2$ gas. $N_2$ gas is also introduced into the reactor 11 via the orifice 15. The $N_2$ gas is dried by a drying agent such as calcium chloride and the like. Reagent bottles 3, 4, 5 and 6 are charged with detrityl, oxidizing, capping and condensation agents respectively. The raw material bottles 7, 8, 9 and 10 are charged with nucleotide reagent/solvent solution having the bases adenine (A), guanine (G), cytosine (C) and thymine (T), respectively.

Check valves 16, 17 and 18 are provided at the inlets of the reagent bottles 3, 4 and 5 respectively for preventing the vapour and mist of the detrityl, oxidizing and capping agents from counterflowing through the passage and from flowing into the other bottles. This is accomplished because mixing of vapour or mist of the detrityl, oxidizing and capping agents with other reagents, solvents and nucleotide reagents deteriorates the function thereof.

Figure 8:
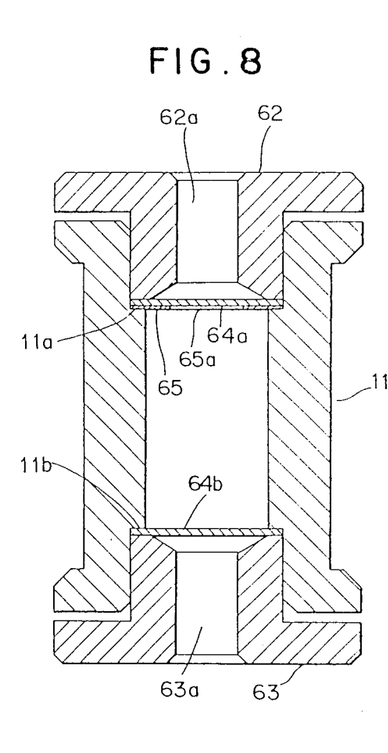

One embodiment of the reactor 11, will be explained with reference to FIG. 8.

The reactor body 11 is made of lucent or translucent synthetic resin or glass, the inner surface of which is subjected to silanation. The body 11 is provided with the stepped portions 11a and 11b at the openings of the upper and lower ends thereof respectively.

Upper and lower plugs 62 and 63 are inserted into the upper and lower end openings respectively. Filters 64a and 64b are interposed between upper and lower plugs 62 and 63 and the stepped portions 11a and 11b respectively.

These filters 64a and 64b can capture the support charged in the reactor body 11 and are made so that they are insoluble in the reagents and solvents required for the polynucleotide synthesis reaction.

At the side of the upper plug 62 (or at the top of the reactor) a non-adhesive sheet 65 having a smooth surface of non-adhesive material such as fluorine resin (typically ethylene tetrafluoride) is interposed between the filter 64a and the stepped portion 11a. The non-adhesive sheet 65 is formed with a hole 65a at the center thereof so that the sheet covers the peripheral edge of the filter 64a.

In accordance with the afore-mentioned embodiment, when the reagents or solvents which have been introduced into the reactor body 11 via the passage 63a of the lower plug 63 overflow the body 11, the support in the reactor body 11 floats upward and is biased toward the filter 64a. At this time the support has a tendency to be deposited on the filter 64a while the non-adhesive sheet 65 prevents this tendency. Accordingly the support will adhere only to the central area of the filter 64a which is not covered with the non-adhesive sheet 65, so that there is no fear that the support will adhere upon the inner peripheral portion of the body 11.

When the reagents having a higher specific gravity are introduced into the body 11 via the passage 63a of the lower plug 63, the support will also float upward and is biased against the filter 64a while adherence to the filter 64a is prevented similarly.

Although the afore-mentioned embodiment shows that the peripheral edge of the filter 64a is covered with the non-adhesive sheet 65, the filter may be formed integrally with a non-adhesive layer at the peripheral edge thereof.

Referring again to FIG. 1, a solenoid valve 19 is provided at the passage 14. Solenoid valves 20 to 28 are provided at the outlet of each of the bottles 2 to 10 respectively.

Solenoid valves 29, 30, 31 and 31' are provided at the bottom and top sides of the reactor 11. The valves 19 to 31' are controlled to be opened or closed by means of the afore-mentioned control means 12.

Figure 5A:
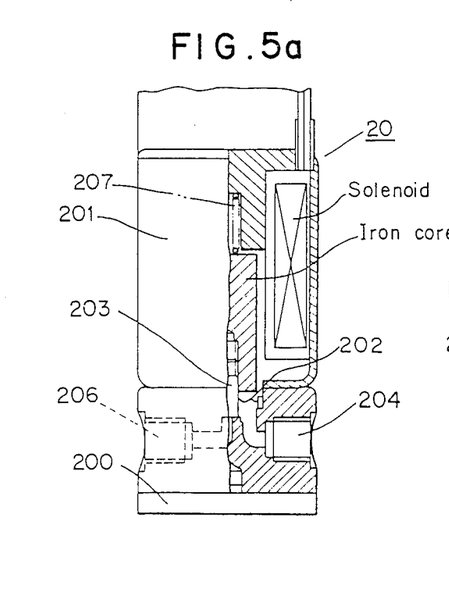
FIG. 5a is a front view, partly in cutaway, showing a solenoid valve.
Figure 5B:
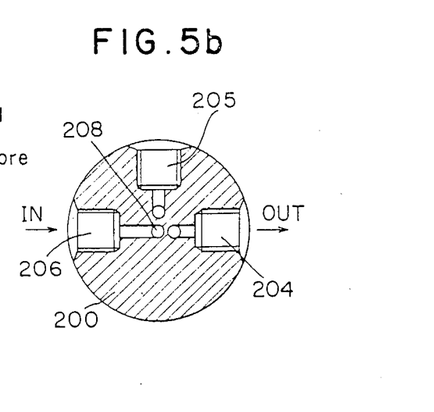
FIG. 5b is a sectional view showing a valve body.

The solenoid valve 19 is a two-directional valve and is opened when the solenoid (not shown) is energized, and closed by the biasing force of a spring (not shown) when not energized. The structure of the solenoid valve 19 is identical with that of the three-directional valve of FIG. 5 except for that port 205 is eliminated.

The solenoid valves 20 to 28 are three-directional valves and have structures identical to each other. The solenoid valve 20 is shown in detail in FIGS. 5a and 5b.

The solenoid valve 20 comprises a valve body 200 and a valve rod 203 which is supported by a solenoid 201 and a diaphragm 202. The valve body 200 is provided with ports 204 and 205 which are normally opened and a port 206 which is brought into communication with the ports 204 and 205 only when the solenoid is energized.

When the solenid 201 is energized, the valve rod 203 is retracted against the biasing force of the spring 207 so that the ports 204, 205 and 206 are brought into communication with each other. When deenergized, the valve rod 23 is extended by the biasing force of the spring 207 to cut off the communication between the port 204, 205 and the ports 206.

The port 206 is brought into communication with with the outlet of the solvent bottle 2 shown in dotted line of FIG. 1. The normally communicated ports 204 and 205 are communicated with the ports of the other solenoid valves 21 to 28, which are normally opened (refer to solid line in FIG. 1). $N_2$ gas, solvent and the like are fed to the reactor 11 via the normally opened ports of the respective solenoid valves 20 to 28.

The solenoid valves 29, 30, 31 and 31' are three-directional valves and have an identical structure. These valves are switched to a position shown in dotted line in FIG. 1 when the solenoid (not shown) is energized while they are switched to a position of solid line in FIG. 1 when deenergized.

The connection of the solenoid valves provided at the outlet of the respective bottles will be described. The afore-mentioned first, second and third ports 204, 205 and 206 respectively (connected at the outlet of the bottles) are disposed along the periphery of the valve body of the solenoid valve in a given angular relationship. The first port is normally in communication with the second port. The third port is communicated with the first and second ports. The first and second ports of the respective solenoid valves are disposed so that they are adjacent each other and are at a lower position. The first and second ports are communicated with each other via a tube so that the axis of the first port and the axis of the second port adjacent to the first port are inclined with respect to the vertical axis (horizontal axis).

Figure 9A:
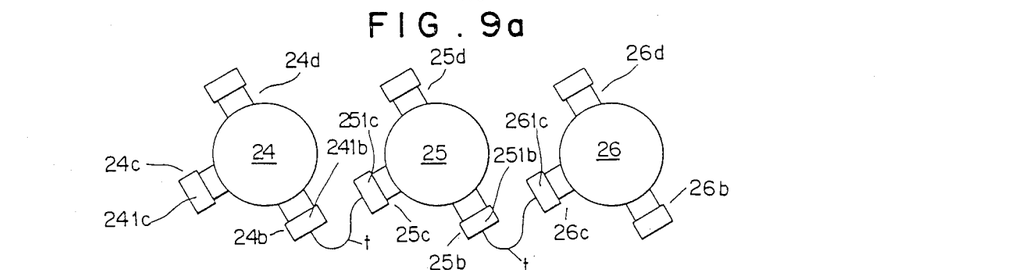
FIGS. 9a and 9b are schematic views showing the arrangements and connections of the solenoid valves.
Figure 9B:
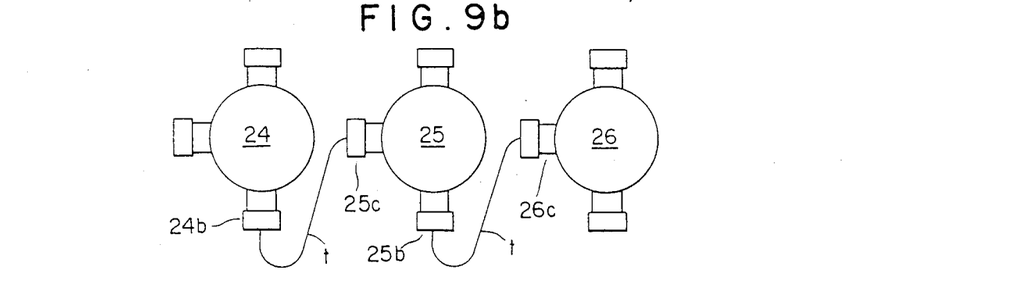

FIG. 9a shows the connection of the solenoid valves 24 to 26 on an enlarged scale. It is apparent from FIG. 9a that the solenoid valves 24 to 26 can be disposed in a close relation with each other without causing the tube fittings 241b and 251b disposed at the ports 24b and 25b of the solenoid valves 24 and 25 to interfere with the tube fittings 251c and 261c disposed at the ports 25c and 26c of the solenoid valves 25 and 26 and that the valves may be connected so that the sagging of the tubes t is reduced as small as possible. Although the solenoid valves 24 to 26 have been exemplified it is apparent that the solenoid valves 20 to 23, 27 to 31 and 31' may be similarly connected. On the other hand when the valves 24 to 26 are assumed to be connected with the ports 24b and 25b disposed along the vertical line 1 (angle with respect to the vertical line is 0, that is at a position of 6 o'clock) and the ports 25c and 26c are disposed along the horizontal line (angle with respect to the horizontal line is 0, that is, at a position of 9 o'clock), the tubes t would be largely sagged although the solenoid valves 24 to 26 may be connected in a close relationship with each other.

The angle of the axis of the ports 20b to 28b with respect to the vertical line may be 60 to minus 15 degrees (30 to 50 degrees with respect to the horizontal line), preferably in a range of 45 to 105 degrees. For example, when the axes of the ports 20b to 28b are at about 45 degrees with respect to the vertical line and the axes of the ports 20c to 28c are at about 45 degrees with respect to vertical line, the sagging of the tubes t may be made even smaller although the ports 20b to 28b are at a position slightly higher than that of the shown embodiment. Such an arrangement makes the sagging of the tubes smaller and the apparatus more compact.

The control means 12 which is a primary the feature of the present invention will be described. The control means 12 comprises a programmable controller 32. The programmable controller 32 is made of semiconductor elements such as IC and LSI which are replaced with the contact magnetic relays used in prior art control circuit. The programmable controller comprises an arithmetic control unit 33, a storage unit (system memory) 35 in which a grammer (system program) of arithmetic and control system in the arithmetic unit is stored, a storage unit (user memory) 34 in which a user program is stored which is designed so that the user of the programmable controller 32 can receive and transmit the input and output signals with external devices as he desires and input and output devices (not shown).

The programmable controller 32 is connected with a basic sequence input unit 36 which appoints a base sequence.

The base sequence input unit 36 comprises an input key 37 and a microprocessor 38.

The CPU of the arithmetic control unit 33 includes for example a 8061, 8085, 6008 type IC. The user memory of the storage unit 34 includes a memory device such as 2 to 32 k bit ROM, PROM, EPROM and the like. The storage unit 34 is, for example, a memory pack and may be removably mounted on a memory pack receiving portion (not shown) of the housing of the programmable controller 12. The system memory used for the storage unit 35 includes 32-96 k bit ROM or PROM. A timer/counter includes a 30 to 200 counter and the input/output marks are 20 to 64 in total.

Figure 3:
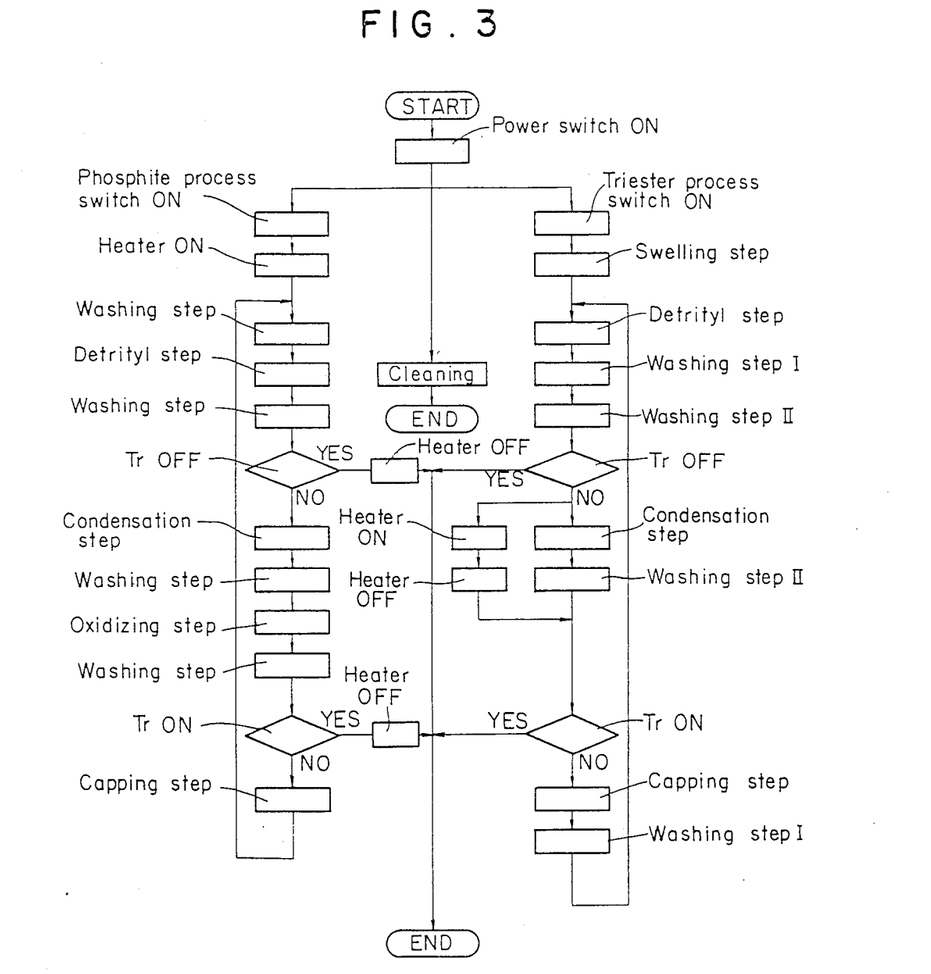
FIG. 3 is a flow chart showing the operation of the present apparatus.

The content of a flow chart shown in FIG. 3 is stored in the storage unit 34. A program for washing and drying the entire synthesizing apparatus, which starts from a condition that a washing solvent has been charged in respective bottles in also stored.

A memory pack device, in which the storage unit 34 comprises semiconductor memory such as ROM (Read Only Memory), PROM (Programmable Read Only Memory), EPROM (Erasable Programmable Read Only Memory) in which the other device control program and/or program for product shipment test and maintainance operation test is stored, is set on the memory pack container so that the memory pack device may be replaced with the storage unit of the programmable controller from the outside of the housing. Specifically the afore-mentioned program includes a program for testing the operation of the microprocessor 38, a program for testing a sheet leakage of the solenoid valves 20 to 31' and $N_2$ flow rate, a program for test testing whether or not the tubes are properly connected, a program for testing the amount of flow of the solvent, reagent and raw material, and a program for testing each of the solenoid valves 20 to 31'.

FIG. 2 illustrates a peripheral circuit of the programmable controller. In the drawings, reference numeral 40 is a rectifier, 41a to 41m are output relays, 42 is a begin switch, 43 is a temporal stop switch, 44 is a continuation switch, 45 is a trityl OFF switch, 46 is a trityl ON switch, 46' is a file-up switch, 47 is a cleaning switch, 48 is a phosphite process switch, 49 is a triester process switch, 50a to 50n are input units, and 51a to 51c are output units.

The output relays 41a to 41m are connected with the solenoid valves 19 to 31' and energize the solenoid valves 19 to 31' when their contacts are closed.

The begin switch 42 starts the operation of the programmable controller 32 and the microprocessor 38. The temporal stop switch 43 serves to temporarily stop the operation of the programmable controller 32 and microprocessor 38. The continuation switch 44 restarts the programmable controller 32 and the microprocessor 38 from the temporal stop condition.

The trityl OFF switch 45 serves to operate the programmable controller 32 so that the reaction will be completed under the condition that the protection group is removed and to operate the programmable controller 32 so that the reaction will be completed under the condition that the protection group is added.

The output relays 41n to q and indicator lamps 54 to 57 serve to indicate detrityl, condensation, oxidizing and capping processes.

The cleaning switch 47 serves to operate the programmable controller 32 so that solvent solutions are charged into the solvent, reagent and nucleotide reagent bottles and each of the bottles, reactor 11 and the passage are washed. The fill-up switch 46' serves to operate the programmable controller 32 so that the passages between the bottles 2 to 11 and the solenoid valves 20 to 28 are filled with solvents and the like prior to starting of reaction operation.

The output terminals 38a to 38e and input terminals 38f to 38h of the microprocessor 38 are connected with the input units 50h to 50l and the output units 38a to 38e respectively. When an increment signal is generated from the output unit 51a to the input terminal 38f, the data on next address of the storage of the microprocesor 38 is displayed on a microprocessor display and simultaneously a data signal of adenine (A), guanine (G), cytosine (C), thymine (T) are output from the input terminals 38a to 38e to the input units 50h to 50l respectively. When the controller is started by the begin switch, a signal is input from 51b to 38g and the initial address of the storage of the controller 32 is displayed and the data signal on the intitial address is output to 50h to 50l. When the controller is restarted by the continuation switch, a signal is output from 51c to 38b and the current address of the storage of the controller 32 is displayed and the data signal is output to 50b to 50l.

Reference numeral 52 in the drawing represents a pressure gauge of $N_2$ gas.

Figure 7:
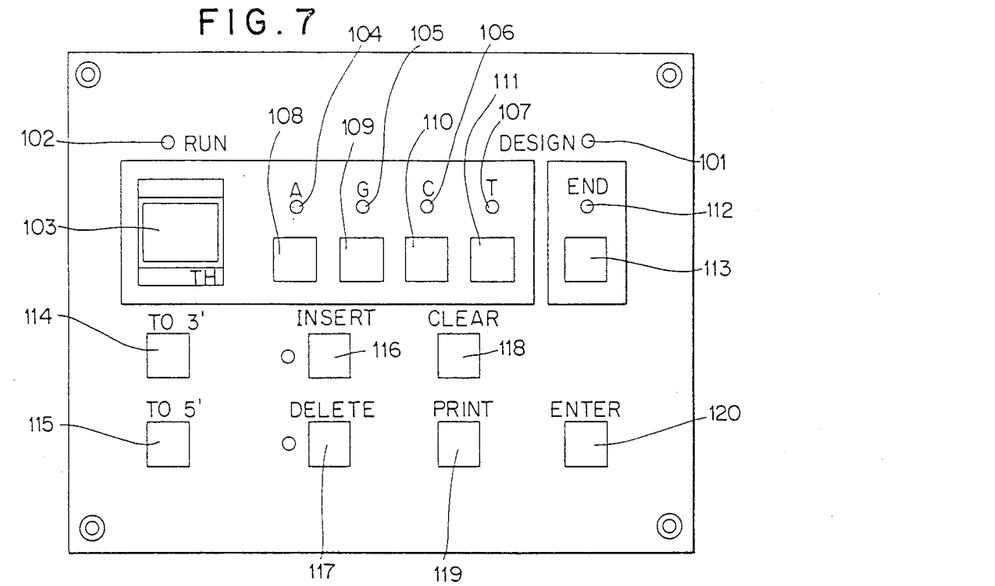
FIG. 7 is a front view showing input and display units of the microprocessor.

FIG. 7 is a front view showing the input and display of the microprocessor 38. The microprocessor 38 is designed to function as both a base sequence input device and an input data display while a DESIGN lamp 101 at the right and upper end lights and functions as both a supply device for supplying the base sequence data and END data while exchanging input and output signal with the programmable controller and a display device which displays what base of the growing terminal group of the polynucleotide is currently synthesized in the reactor.

An address display which displays the nth position from the synthesis initiating terminal (usually 3' terminal) of the polynucleotide is condensed comprises two digits of 7 segment character. The indication lamps 104 to 107 which indicate one of bases A, G, C, T of the nucleotide which is to be condensed and the input switches 108 to 111 are made one set. An END lamp 112 which indicates a terminal where the synthesis finishes and the END input switch 113 are made one set. Furthermore, a switch 114 for moving the address display in a direction toward the synthesis starting terminal and a switch 115 for moving the address display toward the synthesis finish terminal are provided. A switch 116 for insertion of the address and the data, a switch 117 for deletion and their function indication lamps 121, 122 are provided. A switch 118 for clearing the address data and for clearing the insertion and deletion switches, a switch 119 for printing out the base sequence of polynucleotide which is presently stored and a switch 120 for transferring the temporary register of the address, END and base and the like to a register and data of the control unit 12 to the storage are provided.

The operation of the afore-mentioned embodiment will be described with reference to a flow chart of FIG. 3.

A porous glass support with which thymine nucleotide (T) is bonded is charged into the reactor 11. The power switch 39 is turned on. If the reaction will be performed in accordance with the phosphite process, the phosphite process switch 48 is pressed. This causes the programmable controller 32 to execute the control program set forth at left column in FIG. 3. A heater (not shown) is turned on to heat the reactor 11 to 20°–22° C. Washing with a solvent (acetonitrile) is then carried out. In this washing step, solvent (acetonitrile) is introduced into the reactor 11 via the bottom thereof from the bottle 2 under pressure of $N_2$ gas by opening the solenoid valve 20. Then the solvent left in the passage is introduced into the reactor 11 under pressure of $N_2$ gas by opening the solenoid valve 19. Bubbling is carried out in the reactor 11. On bubbling, the solenoid valves 19, 29 are intermittently opened or alternatively the solenoid valve 29 is intermittently opened while the solenoid valve 19 is continued to open so that $N_2$ gas under a pressure of 0.1 kg/cm$^2$ to 1.0 kg/cm$^2$ is blown for 0.02 sec. to 2.0 sec. The blowing is stopped for a predetermined period of time. These steps are repeated. Intermittent blowing of $N_2$ gas in such a manner results in an agitation effect due to bubbling. Furthermore, generation of mist and evaporation of solvent is suppressed. If the period of time for $N_2$ gas blowing is shorter than 0.02 sec., agitation effect would not be obtained. If the period of time for $N_2$ gas blowing is longer than 2.0 sec. mist would be formed. Thereafter the solenoid valves 29, 30 are switched to a position represented in dotted line. The solvent is discharged from the reactor 11 by blowing $N_2$ gas from the top of the reactor 11. This operation is repeated a plurality of times.

Detritylation step is then carried out. At this detritylation step, detrityl agent (3% trichloro acetic acid/methylene chloride solution) is introduced from the bottle 3 into the reactor 11 via the bottom thereof under pressure of $N_2$ gas by opening the solenoid valve 21. The following operation is carried out in the same manner as the washing step. This operation is repeated a plurality of times. During this detritylation step, the solenoid valve 31 is opened to discharge the discharged liquid to a sample tube set to a fraction collector.

Figure 4:
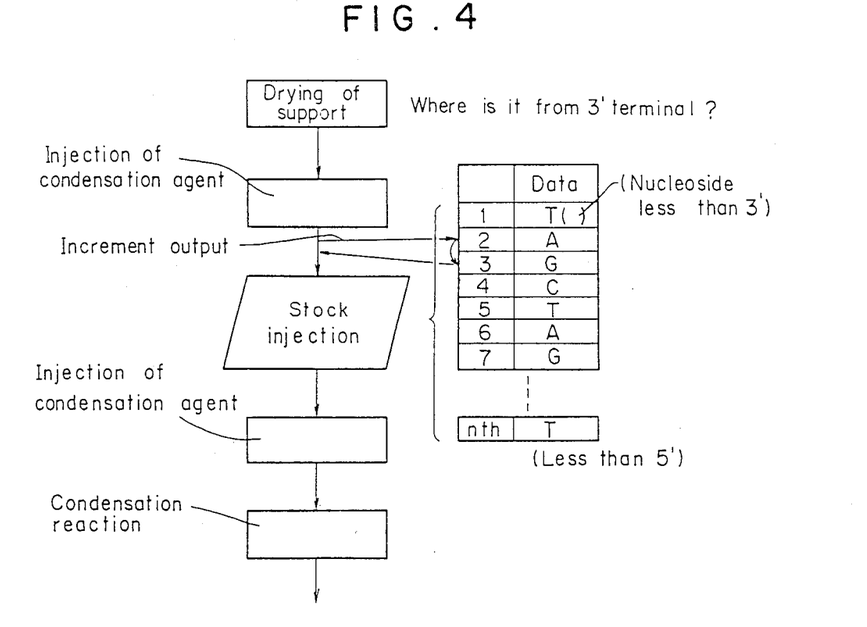
FIG. 4 is a flow chart showing a condensation step in detail.

Thereafter the washing step is carried out again. The operation proceeds to condensation step except for the case when the END input is provided from the microprocessor 38 and the trityl OFF switch 45 is turned on. The condensation step at which an increment pressure is provided from the programmable controller 51a to the microprocessor 38 and the fraction collector to increment them comprises the steps of a condensation agent (tetrazole/acetonitrile solution) charging step (I) after drying of the support by $N_2$ gas, the nucleotide reagents (phosphoramidite) charging step, a condensation agent (tetrazole/acetonitrile solution) charging step (II), and a condensation reaction step. At the condensation agent charging step (I) the condensation agent equal to half of the required amount is introduced to the reactor 11. At the condensation agent charging step (II), the remaining condensation agent is introduced. At the nucleotide reagents (phosphoramidite) charging step, operation is carried out in accordance with an instruction from the base sequence input unit 36. For example, nucleotide amidite reagent/solvent (acetonitrile) solution, said nucleotide amidite having as base adenine which is a nucleotide base to the firstly bonded is introduced from the bottle 7 to the reactor 11 which is charged with a support which thymine nucleoside (T) is bonded by opening the solenoid valve 25 at first condensation process. Nucleotide-amidite reagent/solvent (acetonitrile) solution, said nucleotide-amidite having as base quanine (G), cytosine (C), thymine (T), adenine (A) . . . thymine (T) are introduced to the reactor 11 at second, third, fourth, fifth . . . and nth condensation steps respectively. During condensation reaction, it is possible to sample the reaction liquid from the reactor 11 and to check the promotion of the reaction by energizing the solenoid valves 29, 30, 31 to change to the position shown in dotted line in FIG. 1.

In this case, the previous address and data is displayed until an increment signal is output. When the increment signal is output, a next address is displayed and the data on this address is output to the programmable controller 32.

Two, three and four kinds of nucleotide reagents may be simultaneously fed to the reactor 11. When the n kinds of nucleotide reagents are supplied, the opening period of time for valves 25 to 28 is set to 1/n of that in the case when the one nucleotide reagent is supplied. A dimer nucleotide reagent or a trimer nucleotide reagent may be charged into a raw material bottle and then fed to the reactor 11.

After completion of the afore-mentioned condensation step, an oxidizing step is carried out through a washing step. At this oxidizing step, an oxidizing agent (iodine water/diaxane solution) is introduced into a bottle 11 under pressure of $N_2$ gas by opening the solenoid valve 22. Thereafter operation is carried out in the same manner as the washing step. This operation is repeated a plurality of times. After completion of oxidizing step washing is carried out. The process proceeds to the capping step except for the case when the END signal is input to the microprocessor 38 and the trithyl ON switch 46 is turned on. At this capping step, the solenoid valve 23 is opened to feed the capping agent from the bottle 5 to the reactor 11 under pressure of $N_2$ gas. Thereafter operation is carried out in the same manner as washing step. This operation may be repeated a plurality of times.

After completion of the capping step, operation is repeated again from the washing step. If the data on the base and END signal are input to a new address of the storage of the base sequence input unit 36, the synthesis operation would be completed while the protection group is removed or added after the synthesis reaction of the appointed last base finishes. When the synthesis reaction is desired to finish while the protection group is removed, the trityl OFF switch is turned on. When the synthesis reaction is desired to finish while the protection group is added.

It is also possible to carry out a step for cutting out polynucleotide from the reactor 11 after completion of the synthesis operation. A reagent bottle for the cutting out step may be provided. However, since the cutting out step is not a repetition step and this step takes a long period of time to carry out, the efficiency is not high.

When the reaction is carried out in accordance with the triester process, the reagent bottle 4 may be empty since the oxidizing agent is not used unlike the phosphite process. Alternatively, the reagent bottle may be used as a solvent bottle 4 containing a solvent II which is contained in bottle 2 or different solvent II. Other example in which different solvent is used will be described. The triester process switch 49 is turned on. This causes the control content set forth in the right column of FIG. 3 to be executed by the programmable controller 32. When polystyrene gel is used for the support, a swelling step is required. The support is swelled with methylene chloride/methanol mixed liquid (solvent I). The process is identical with the phosphite process except that the oxidizing step is not required. At the washing step after detritylation, the support is washed with methylene chloride/methanol mixed liquid once and then washed with tetrahydrofuran anhydride solvent twice and then is dried with $N_2$ gas. Tetrahydrofuran anhydride is used for washing after condensation step. Methylene/methanol mixed liquid is used for washing after capping step.

If the temporal stop switch 43 is turned on or the operation of the programmable controller 32 is stopped due to power failure while the synthesis is carried out, the condition immediately before the turning on the switch 43 or power failure is held. The operation is continued when the continuation switch 46 is turned on or the power is recovered.

In the afore-mentioned embodiment, the solenoid valves 20 to 28 are provided only at the outlet of the bottles 2 to 10 so that the pressure of $N_2$ gas is normally applied to the bottles 2 to 10. Accordingly decrease in pressure seldom occurs even when the $N_2$ gas is slightly leaked from the bottles 2 to 10. Liquid supply is carried out simulteneously with opening of the solenoid valves 20 to 28.

Since check valves 16, 17 and 18 are provided at the outlets of the bottle 3 containing a detrityl agent, the bottle 4 of the solvent II and the bottle 5 of the capping agent respectively, there is no fear that the vapor of the mist of these reagents will counterflow the passage 14 to enter the other bottles.

In the case that solenoid valves are provided instead of check valves 16, 17 and 18 and they are adapted to be opened simutaneously with opening of the solenoid valves 21, 22 and 23, slight leakage of $N_2$ gas from the bottles 3, 4 or 5 would result in decrease in pressure. Liquid supply would be carried out after increase in pressure when the solenoid valves are opened. If the flow rate is controlled in response to opening time of the solenoid valve, disadvantages such as reduced flow rate would occur. A filter is provided at the outlet from respective bottle to the valve, thereby preventing leakage due to introduction of foreign material into the valve.

The solenoid valve 31' is a precut valve which is used when slight leakage should occur in the bottles 20 to 31, or when it is desired to eliminate the possibility of leakage in the valves 20 to 30, or any factor lowering the yield such as influence of deterioration of reagent in the course of synthesis of very long polymer. When the liquid is fed to the reactor at a few points in the reaction course, initial 0.1-0.5 ml of a preset amount of the liquid may be discharged from the system without being introduced to the reactor. When the valves 20, 30 and 31' are simultaneously changed to a mode represented in dotted line by turning them on, the system is closed while it is filled with N₂ gas. The leakage in the solenoid valves 20 to 28 may be prevented due to absence of a differential pressure between respective port in the solenoid valves 20 and 28 during this time.

Figure 6:
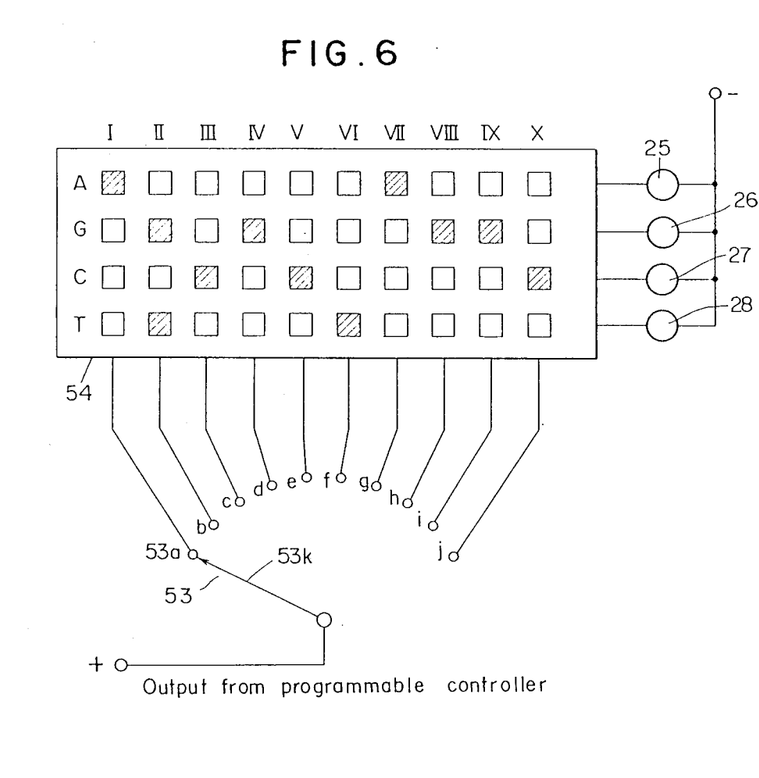
FIG. 6 is a schematic view showing another example of the base sequence input unit.

FIG. 6 shows the other embodiment of the base sequence input unit 36 in which a rotary switch 53 and a program board with push button type diode switches are used in lieu of the microprocessor 38.

One of the output relays of the programmable controller is turned on when nucleotide is supplied. The movable contact 53k of the rotary switch 53 which is operatively connected with the relay, is successively switched to stationary contacts 53a to 53j. At the first synthesis reaction, the solenoid valve 25 is opened so that a nucleotide (having adenine (A) as base) reagent/solvent solution is fed to the reactor 11. At the second synthesis reaction, the solenoid valves 26 and 28 is opened so that nucleotide (having guanine (G) as base) reagent and nucleotide (having thymine as base) reagent is fed to the reactor. At the third synthesis the solenoid valve 27 is opened so that nucleotide having cytosine (C) as base is fed to the reactor.

In the afore-mentioned embodiment, all the reagents including condensation agent, nucleotide reagent are automatically fed to the reactor 11. However, the apparatus may be modified so that condensation agent and nucleotide reagent are manually injected. In this case, base sequence input unit 36 is not necessary.

The present apparatus may be used for the synthesis of RNA as well as the synthesis of DNA.

Since the liquid supply and discharge means (solenoid valves 19 to 31) are controlled in accordance with the stored contents of a storage unit by means of a programmable controller including the storage unit in which the supply amount of the liquids such as reagent, solvent and the like and liquid supply and discharge sequences are stored as mentioned above, no interfaces are required and incorporation of the controller mounted on the housing is not necessary, thereby enabling reduction in cost and size of the entire apparatus. Furthermore the present apparatus does not require sophisticated operation and a long period of standby time due to the fact that there are too many input data and selection branches which are found in conventional microcomputer incorporated apparatus. Even a beginner can easily operate the apparatus.

Furthermore, the controlled contents can be readily changed by changing the stored contents in the storage unit or the appointed contents in the base sequence input unit, thereby enabling to improve the operability.

If the base sequence input unit comprises a microprocessor substantially same function as those of the entire control device comprising a microcomputer may be obtained, and reduction in cost can be accomplished. The microprocessor forming only the base sequence input unit can not only be made of economical semiconductor elements, but also key board becomes compact and economical. Furthermore the apparatus may be used without changing the specification irrespective of the modification of main control unit or user memory and change in apparatus type, the apparatus can economically respond to improvements in apparatus type and chemical reaction.

What is claimed is:

1. A polynucleotide synthesizing apparatus, comprising:
   a storing section for storing fluid chemicals necessary for polynucleotide synthesis;
   a reactor in which said fluid chemicals react to effect polynucleotide synthesis, said reactor having an inlet and an outlet;
   fluid supply and discharge means for supplying fluid chemicals in said storing section to said reactor and for discharging said fluid chemicals from said reactor;
   control means for controlling said fluid supply and discharge means, said control means comprising a programmable controller including a storage unit in which supply amount and supply/discharge sequence information for said fluid chemicals is stored;
   a base sequence input unit connected with said programmable controller and containing information for controlling a supply order of raw materials to said reactor, said fluid supply and discharge means being controlled by said information in said storage unit and said information in said base sequence input unit;
   an address display which represents a position from a synthesis initiating terminal of a nucleotide;
   a plurality of base indicating lamps which indicate a type of nucleotide base;
   a control unit which controls said address display and base indicating lamps in response to base sequence data in said storage unit; and
   a memory pack comprising semiconductor memory devices in which a control program and/or maintenance program is stored, said memory pack being replaceable with said storage unit of said programmable controller.

2. A polynucleotide synthesizing apparatus as claimed in claim 1, in which said storing section includes a plurality of solvent bottles and reagent bottles containing solvents and reagents respectively, each solvent and reagent bottle having a passage at an inert gas inlet side thereof, said passage of each solvent bottle and each reagent bottle being provided with a check valve for preventing counterflow of chemicals into other solvent and reagent bottles.

3. A polynucleotide synthesizing apparatus as claimed in claim 1, wherein said reactor has a reactor body provided with filters at top and bottom sides thereof, a support holding raw materials thereon and disposed between said filters, and a non-adhesive portion provided along a peripheral edge of the filter at said top side to prevent said support from adhering to said filter.

4. A polynucleotide synthesizing apparatus as claimed in claim 1, in which a solenoid valve is provided at said inlet and outlet of said reactor, said solenoid valve comprising a valve body provided with a valve opening and a valve rod which opens and closes the valve opening in response to a piston in said solenoid valve, said valve opening communicating with a port at a communication space which communicates with a plurality of ports.

5. A polynucleotide synthesizing appratus as claimed in claim 4, in which a first outlet port having an axis, a second inlet port having an axis and a third port connected with an outlet side of said storing section are provided along a periphery of said valve body at a given angle; said first and second ports being normally in communication with each other, said third port being in communication with said first and second ports when energized, said first and second ports being disposed so that they are positioned at a lower position and adjacent to each other, said first port being in communication with said second port via a tube so that said axis of said first port and said axis of said second port adjacent to said first port are inclined with respect to a vertical axis.

6. A polynucleotide synthesizing apparatus as claimed in claim 1, in which said semiconductor memory devices are selected from a ROM, a PROM and an EPROM.

* * * * *